US012746234B2

(12) United States Patent
Hua et al.

(10) Patent No.: US 12,746,234 B2
(45) Date of Patent: Sep. 29, 2026

(54) USE OF COMPOSITION CONTAINING CILOSTAZOL IN CEREBROVASCULAR DISEASES

(71) Applicant: NEURODAWN PHARMACEUTICAL CO., LTD., Nanjing (CN)

(72) Inventors: Yao Hua, Nanjing (CN); Lei Wang, Nanjing (CN); Zhengping Zhang, Nanjing (CN); Rong Chen, Nanjing (CN); Shibao Yang, Nanjing (CN)

(73) Assignee: NEURODAWN PHARMACEUTICAL CO., LTD., Nanjing (CN)

( * ) Notice: Subject to any disclaimer, the term of this patent is extended or adjusted under 35 U.S.C. 154(b) by 544 days.

(21) Appl. No.: 18/263,191

(22) PCT Filed: Jan. 26, 2022

(86) PCT No.: PCT/CN2022/073910
§ 371 (c)(1),
(2) Date: Jul. 27, 2023

(87) PCT Pub. No.: WO2022/161376
PCT Pub. Date: Aug. 4, 2022

(65) Prior Publication Data

US 2024/0122917 A1 Apr. 18, 2024

(30) Foreign Application Priority Data

Jan. 29, 2021 (CN) ......................... 202110122555.3

(51) Int. Cl.
*A61K 31/4709* (2006.01)
*A61K 31/4152* (2006.01)
*A61P 9/10* (2006.01)

(52) U.S. Cl.
CPC ...... *A61K 31/4709* (2013.01); *A61K 31/4152* (2013.01); *A61P 9/10* (2018.01)

(58) Field of Classification Search
CPC .... A61K 31/4709; A61K 31/4152; A61P 9/10
See application file for complete search history.

(56) References Cited

U.S. PATENT DOCUMENTS

2009/0297596 A1 12/2009 Devane et al.

FOREIGN PATENT DOCUMENTS

CN 102485223 A 6/2012
CN 106913570 A 7/2017

OTHER PUBLICATIONS

Adibhatla, R. et al., "Brain poster session: experimental cerebral ischemia—in vitro," *Journal of Cerebral Blood Flow & Metabolism*, 29 (2009): S155-S165.

Extended European Search Report issued in European Patent Application No. 22745250.5, dated Mar. 18, 2024.

Suzuki, Y. et al., "Hemichorea in a diabetes mellitus patient following acute ischemic stroke with changes in regional cerebral blood flow," *Journal of the Chinese Medical Association*, 78 (2015): 188-191.

"Twenty-third Meeting of the European Neurological Society, Jun. 8-11, 2013, Barcelona, Spain," *Journal of Neurology*, 260.Suppl. 1 (2013): S1-S280.

English Translation of First Office Action issued in Chinese Patent Application No. 202110122555.3, issued Aug. 31, 2023.

Yan, J. et al., "Pharmacological effects of Cilostazole and its application in ischemic stroke," *Chinese Pharmacy*, 23.20 (2012): 1916-1918. (English abstract).

Matsumoto, M., "Cilostazol in secondary prevention of stroke: Impact of the Cilostazol Stroke Prevention Study," *Atherosclerosis Supplements*, 6 (2006): 33-40.

Office Action issued in Japanese Patent Application No. 2023-543219, dated Jul. 30, 2014.

Ikeda, S. et al., "Effects of Edaravone, a Free Radical Scavenger, on Photochemically Induced Cerebral Infarction in a Rat Hemiplegic Model," *The Scientific World Journal*, (2013): 1-5.

Kimura, T. et al., "Ultra-Early Combination Antiplatelet Therapy with Cilostazol for the Prevention of Branch Atheromatous Disease: A Multicenter Prospective Study," *Cerebrovascular Diseases*, 6 (2016): 84-95.

Ohta, Y. et al., "Efficacy of the Free Radical Scavenger, Edaravone, for Motor Palsy of Acute Lacunar Infarction," *Internal Medicine*, 48 (2009): 593-596.

PCT International Search Report and Written Opinion issued in International Patent Application No. PCT/CN2022/073910, mailed Apr. 1, 2022.

Wanatabe, T. et al., "Research and Development of the Free Radical Scavenger Edaravone as a Neuroprotectant," *The Pharmaceutical Society of Japan*, 124 (2004): 99-111.

Wu, Y. et al., "Protection of Cilostazol on Cultured Brain Microvascular Endothelial Cells Deprived of Oxygen and Glucose in Rats," *Journal of Apoplexy and Nervous Diseases*, 27 (2010): 898-901.

Yamamoto, Y. et al., "A Combined Treatment for Acute Larger Lacunar-Type Infarction," *Journal of Stroke and Cerebrovascular Diseases*, 20 (2011): 387-394.

(Continued)

*Primary Examiner* — Timothy R Rozof
(74) *Attorney, Agent, or Firm* — pH IP Law

(57) ABSTRACT

Disclosed is the use of a composition containing cilostazol or a pharmaceutically acceptable salt thereof and edaravone in the preparation of a drug for treating cerebrovascular diseases, especially ischemic cerebrovascular diseases. The experiment result shows that the tail vein administration of 1-15 mg/kg of cilostazol or 1.67-8.33 mg/kg of edaravone on rats with a focal cerebral ischemia-reperfusion injury can significantly ameliorate neurological defects in rats with an MCAO and reduce a cerebral infarction area; and performing compound combination within the dosage range (the mass ratio of cilostazol:edaravone is 1:5 to 5:1) can be synergistic. The tail vein administration of 3.33-16.67 mg/kg of cilostazol or 3.33-16.67 mg/kg of edaravone on mice with a focal cerebral ischemia-reperfusion injury can significantly ameliorate neurological defects in mice with an MCAO and reduce a cerebral infarction area.

11 Claims, No Drawings

(56) References Cited

OTHER PUBLICATIONS

Examination Report issued in Australian Patent Application No. 2022212142, dated Feb. 26, 2025.

Nagai, N. et al., "Intravenous Administration of Cilostazol Nanoparticles Ameliorates Acute Ischemic Stroke in a Cerebral Ischemia/Reperfusion-Induced Injury Model," *International Journal of Molecular Sciences*, 16 (2015): 29329-29344.

Jin, Z-j. et al., "Addition in Drug Combination," *Acta Pharmacologica Sinica*, 1.2 (1980): 70-76. (with English abstract).

USE OF COMPOSITION CONTAINING CILOSTAZOL IN CEREBROVASCULAR DISEASES

CROSS REFERENCE TO RELATED APPLICATIONS

This is a US National Phase application under 35 U.S.C. § 371 of International Application No. PCT/CN2022/073910, titled "USE OF COMPOSITION CONTAINING CILOSTAZOL IN CEREBROVASCULAR DISEASES", filed on Jan. 26, 2022, which claims the priority to Chinese Patent Application No. 202110122555.3, titled "USE OF COMPOSITION CONTAINING CILOSTAZOL IN CEREBROVASCULAR DISEASES" filed on Jan. 29, 2021 with the China National Intellectual Property Administration, which are incorporated herein by reference in their entireties.

FIELD

The present invention belongs to the field of pharmacy, and relates to use of a composition of cilostazol and edaravone in the manufacture of a medicament for treating cerebrovascular diseases, in particular ischemic cerebrovascular diseases.

BACKGROUND

Cerebrovascular disease (CVD) refers to brain lesions caused by various cerebrovascular diseases, and can be divided into acute cerebrovascular disease (stroke) and chronic cerebrovascular disease according to its pathogenesis process. Acute cerebrovascular diseases include transient ischemic attack, cerebral thrombosis, cerebral embolism, hypertensive encephalopathy, cerebral hemorrhage, subarachnoid hemorrhage, etc.; chronic cerebrovascular diseases include cerebral arteriosclerosis, cerebrovascular dementia, cerebral arterial steal syndrome, Parkinson's disease, etc. Ischemic stroke is a general term for brain tissue necrosis caused by insufficient cerebral blood supply due to stenosis or occlusion of cerebral blood supply arteries (carotid artery and vertebral artery). Cerebral ischemia includes four types, transient ischemic attack (TIA), reversible neurological deficit (RIND), stroke in progressive (SIE) and complete stroke (CS). There is no cerebral infarction present in TIA, but there are cerebral infarction of different degrees present in RIND, SIE and CS.

Cilostazol is an anti-platelet aggregation drug, which was first developed and synthesized by Otsuka Pharmaceutical Co., Ltd., Japan, launched in Japan in 1988, approved by FDA in the United States in May 1999 and entered China in 1996. Cilostazol is a selective inhibitor of phosphodiesterase 3 (PDE3). The binding rate of cilostazol to plasma protein is about 95%, and most of cilostazol exist in a relatively stable prototype. Cilostazol has broad-spectrum pharmacological activity and has clinical value for many diseases, such as peripheral thrombotic disease and intermittent claudication. Moreover, cilostazol has the functions of anti-platelet and vasodilation, so that it can prevent the recurrence of circulatory shock and coronary artery stenosis. Studies have shown that PDE3 can inhibit the degradation of cAMP in the circulatory system, increase cAMP in platelets and vascular smooth muscle, inhibit the formation of platelets and promote the proliferation of vascular smooth muscle cells. Cilostazol inhibits the degradation of platelets mainly by affecting the following factors: arachidonic acid, adenosine diphosphate, epinephrine, collagen and fibrinase. At present, some experts believe that cilostazol treatment can be recommended for patients with carotid artery thrombosis, which can treat or prevent cerebral ischemia. Meanwhile, PDE3 can inhibit the production of nitric oxide synthase (NOS), thereby reducing the production of nitric oxide (NO).

Cilostazol has a structure represented by the formula as follows:

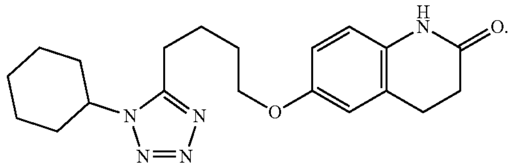

(molecular formula: $C_{20}H_{27}N_5O_2$; molecular weight: 369.47)

Edaravone (chemical name: 3-methyl-1-phenyl-2-pyrazolin-5-one) is a cerebral neuroprotective agent on the market (*Yakugaki Zasshi.* 2004, 124(3): 99-111). Studies have shown that edaravone has antioxidant activity, and can significantly ameliorate the neurological deficit symptoms in animals with cerebral ischemia-reperfusion, reduce the area of cerebral infarction, reduce the degree of brain injury, alleviate cerebral edema, and inhibit lipid peroxidation in damaged brain tissue.

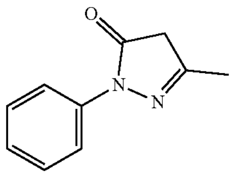

Edaravone (molecular: $C_{10}H_{10}N_2O$; molecular weight: 174.20)

In summary, it is of great practical significance to provide a composition of cilostazol and edaravone for treating cerebrovascular diseases, especially ischemic cerebrovascular diseases.

SUMMARY

An object of the present invention is to provide use of a pharmaceutical composition in the manufacture of a medicament for treating cerebrovascular diseases, wherein the pharmaceutical composition comprises cilostazol or a pharmaceutically acceptable salt thereof and edaravone. Further, the combined use of the pharmaceutical composition can synergistically increase the efficacy of treating cerebrovascular diseases.

In order to achieve the above object of the present invention, the present invention provides the following technical solutions:

In a first aspect, the present invention provides a composition comprising the following components:

component (I), cilostazol, a derivative, a pharmaceutically acceptable salt, or a prodrug molecule thereof; and component (II), edaravone, or a drug with an active ingredient of edaravone.

In some specific embodiments of the present invention, the component (I) and the component (II) are in a weight ratio of 1:10-10:1.

In some specific embodiments of the present invention, the component (I) and the component (II) are in a weight ratio of 1:10-5:1.

In some specific embodiments of the present invention, the component (I) and the component (II) are in a weight ratio of 1:5-10:1.

In some specific embodiments of the present invention, the component (I) and the component (II) are in a weight ratio of 1:5-5:1.

In some specific embodiments of the present invention, the component (I) and the component (II) are in a weight ratio of 1:2.5-2.5:1.

In some specific embodiments of the present invention, the component (I) and the component (II) are in a weight ratio of 1:1-2.5:1.

In some specific embodiments of the present invention, the component (I) and the component (II) are in a weight ratio of 1:1, 5:1, 2.5:1, 1:2.5 and/or 1:5.

In a second aspect, the present invention further provides a drug comprising the composition and a pharmaceutically acceptable adjuvant.

In a third aspect, the present invention further provides use of the composition or the drug in the manufacture of a medicament for preventing and/or treating cerebrovascular diseases;

preferably, the cerebrovascular disease is selected from ischemic cerebrovascular disease;

preferably, the ischemic cerebrovascular disease is selected from ischemic stroke.

The pharmaceutical composition of the present invention can be used in the manufacture of a medicament for cerebrovascular diseases, wherein the cerebrovascular disease is preferably ischemic cerebrovascular disease, more preferably ischemic stroke.

The present invention has the following beneficial effects: according to the results of drug efficacy tests on animals (rats and mice), for cerebrovascular diseases, the combination of cilostazol and edaravone has the effect of synergistically increasing the drug efficacy.

The test results of the present invention show that the administration of cilostazol at 1-15 mg/kg or edaravone at 1.67-8.33 mg/kg in the tail vein of rats with focal cerebral ischemia-reperfusion injury can significantly ameliorate the neurological deficits and reduce the area of cerebral infarction in MCAO rats; and the compounded combination (with a mass ratio of cilostazol:edaravone of 1:5-5:1) within the above dosage range can produce synergistic effect. The administration of cilostazol at 3.33-16.67 mg/kg or edaravone at 3.33-16.67 mg/kg in the tail vein of mice with focal cerebral ischemia-reperfusion injury can significantly ameliorate the neurological deficits and reduce the area of cerebral infarction in MCAO mice.

DETAILED DESCRIPTION

The present invention discloses use of a composition comprising cilostazol in cerebrovascular diseases. Those skilled in the art can refer to the content of this article and appropriately improve the process parameters to realize the present invention. In particular, it should be noted that all similar replacements and modifications are apparent to those skilled in the art, and they are all considered to be included in the present invention. The method and use of the present invention have been described through preferred embodiments, and those skilled in the art can apparently make modifications or appropriate changes and combinations of the method and use described herein without departing from the content, spirit and scope of the present invention to realize and apply the technology of the present invention.

The raw materials and reagents used in the use of the composition comprising cilostazol in cerebrovascular diseases were all commercially available.

The present invention will be further illustrated below in conjunction with examples.

Example 1 Study on the Protective Effect of the Composition of Cilostazol and Edaravone on Focal Cerebral Ischemia-Reperfusion Injury 1

1 Materials and methods 1.1 Experimental Animals

Sprague-Dawley (SD) rats, male, SPF-grade, weighing 250-280 g.

1.2 Test Drugs

| Sample name | Manufacturer | Batch number |
|---|---|---|
| Cilostazol | Shanghai Aladdin Biochemical Technology Co., Ltd. | K1405071 |
| Edaravone | Jiangsu Tiansheng Pharmaceutical Co., Ltd. | 20161103 |

1.3 Experimental Method 1.3.1 Animal Grouping and Administration

The experimental animals were divided into 4 groups, cilostazol group (1 mg/kg), edaravone group (5 mg/kg), cilostazol and edaravone composition group (6 mg/kg, cilostazol:edaravone=1:5, cilostazol 1 mg/kg+edaravone 5 mg/kg) and model group. After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

1.3.2 Establishment of Focal Cerebral Ischemia-Reperfusion Model

The rat focal cerebral ischemia-reperfusion model was established by internal carotid artery suture method. The limbs (hind limbs above the knee joint and forelimbs below the wrist joint) and head of an anesthetized rat were tightened with rubber bands. The animal was fixed on an operating table in supine position, and was shaved with an animal shaver from the head to the chest, and the skin was disinfected with alcohol. The neck of the rat was cut at the midline, and the subcutaneous tissue was bluntly separated. The thin layer of fascia on the surface of the anterior triangle of the neck was separated, the lower side-lower edge of the clavicular hyoid muscle was pulled up, and the longitudinally pulsating artery parallel to this muscle can be seen. The arterial shell was opened, and the bifurcation of the right carotid artery was exposed. The right common carotid artery, external carotid artery and internal carotid artery were separated. The vagus nerve was gently stripped, and the external carotid artery was ligated and cut. The proximal end of the common carotid artery was clamped. An incision was made at the distal end from the ligature of the external carotid artery, and was inserted with a suture line, which was passed through the bifurcation of the common carotid artery into the internal carotid artery, and then was inserted slowly until reaching slight resistance (approximately 20 mm from the bifurcation), so as to block all blood supply to the middle cerebral artery. The suture line was slightly fixed below the incision of the external carotid artery with silk thread. The silk thread clamping the proximal end of the common carotid artery was loosened. A gauze soaked in sterile saline was covered on the wound, and the rat was placed on a heat preservation pad to keep warm. 2.0 h after cerebral ischemia on the right side, the suture line was pulled out gently to restore the blood supply for reperfusion. The external carotid artery was ligated with silk thread fixing the suture line. The skin was stitched, and disinfected. The rats were placed in clean feed, and their general condition and respiration were observed until they woke up from anesthesia. The rats were provided with food and water, and commonly reared.

1.3.3 Determination of the Area of Cerebral Infarction

The animals were subjected to evaluation of neurological deficit symptoms and then sacrificed with $CO_2$. The brain was taken out by cutting off head. The olfactory bulb, cerebellum and lower brainstem were removed. The blood on the surface of the brain was washed with normal saline, and the residual water on the surface was removed. The brain was placed at −20° C. for 20 min, then taken out, immediately cut to a coronal section vertically downward at the crossing plane of the line of sight, and sliced backward every 2 mm. The brain slices were incubated in 1% TTC staining solution (at 37° C. for 30 min). The normal brain tissue was stained into dark red, and the ischemic brain tissue was stained into pale white. After being washed with normal saline, the brain slices were quickly arranged in a row from front to back, removed off the residual water on the surface, and photographed.

Calculation of area of cerebral infarction: The photos were processed by Image J software, and the corresponding area of left brain and non-infarction area of right brain were calculated according to the formula, so that the percentage of the area of infarction was calculated.

Calculation of Volume of Infarction.

$$V=t(A1+A2+A3+ \ldots +An),$$

t is the thickness of a slice, A is the area of infarction.

$$\% I=100\%\times(VC-VL)/VC,$$

% I is the percentage of volume of infarction, VC is the brain volume of the control side (left brain), and VL is the volume of the non-infarction area of the infarction side (right brain).

1.3.4 Analysis of Synergy of Composition

According to Jin Zhengjun's formula q=E(a+b)/(Ea+Eb−Ea×Eb), it was evaluated whether cilostazol and edaravone in the composition had a synergistic effect. In the formula, E(a+b) is the effective rate of combined drugs, and Ea and Eb are respectively the effective rates of drug A (cilostazol) and drug B (edaravone) alone. $E_{administration\ group}=(X_{model}-X_{administration})/X_{model}$, wherein X is the area of cerebral infarction. q value within the range of 0.85 to 1.15 represents a simple addition of the effect of the two drugs used, q value>1.15 represents a synergistic effect, and q value<0.85 represents that the combined use of the two drugs has an antagonistic effect.

1.4 Statistics

Experimental data were expressed as mean t standard deviation (Mean±SD). Differences among groups were analyzed by one-way analysis of variance, comparison between groups was tested by LSD method, and P<0.05 was defined as significant difference.

2 Experimental Results

The effects on the area of cerebral infarction are shown in Table 1. The experimental results show that the administration of edaravone at 5 mg/kg of and the composition (cilostazol 1 mg/kg+edaravone 5 mg/kg) can significantly reduce the area of cerebral infarction in animals (p=0.012, p=0.000), and the administration of cilostazol at 1 mg/kg tended to alleviate cerebral ischemic injury, but showed no statistical difference (p=0.08). The calculation result of synergy was q=1.33, indicating that the combined use of the two drugs had a synergistic effect.

TABLE 1

Effects of combined administration of cilostazol and edaravone on the area of cerebral infarction

| Group | Number of animals | Area of cerebral infarction (%) |
|---|---|---|
| Model group | 11 | 40.35 ± 8.24 |
| Cilostazol group | 11 | 34.24 ± 7.25 |
| Edaravone group | 11 | 29.35 ± 10.45* |
| Group of composition of cilostazol and edaravone in 1:5 | 12 | 19.74 ± 9.30*** |

Mean ± standard deviation,
*p < 0.05,
***p < 0.001, compared with the model group.

Example 2 Study on the Protective Effect of the Composition of Cilostazol and Edaravone on Focal Cerebral Ischemia-Reperfusion Injury 2

1 Materials and Methods 1.1 Experimental Animals

Sprague-Dawley (SD) rats, male, SPF-grade, weighing 250-280 g.

1.2 Test Drugs

Cilostazol and edaravone were the same as in Example 1.

1.3 Experimental Method

The experimental animals were divided into 4 groups, cilostazol group (5 mg/kg), edaravone group (5 mg/kg), cilostazol and edaravone composition group (10 mg/kg, cilostazol:edaravone=1:1, cilostazol 5 mg/kg+edaravone 5 mg/kg) and model group. After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

The establishment of the focal cerebral ischemia-reperfusion model, the determination of the area of cerebral infarction, the analysis of synergy of the composition and the data statistics method were the same as in Example 1.

2 Experimental Results

The effects on the area of cerebral infarction are shown in Table 2. The experimental results show that the administration of cilostazol at 5 mg/kg, edaravone at 5 mg/kg and the composition (cilostazol 5 mg/kg+edaravone 5 mg/kg) can significantly reduce the area of cerebral infarction in animals (p=0.025, p=0.008, p=0.000). The calculation result of synergy was q=1.47, indicating that the combined use of the two drugs had a synergistic effect.

TABLE 2

Effects of combined administration of cilostazol and edaravone on the area of cerebral infarction

| Group | Number of animals | Area of cerebral infarction (%) |
|---|---|---|
| Model group | 11 | 40.50 ± 8.51 |
| Cilostazol group | 12 | 32.59 ± 7.15* |
| Edaravone group | 11 | 29.49 ± 9.06** |
| Group of composition of cilostazol and edaravone in 1:1 | 12 | 15.82 ± 7.43*** |

Mean ± standard deviation,
*p < 0.05,
**p < 0.01,
***p < 0.001, compared with the model group.

Example 3 Study on the Protective Effect of the Composition of Cilostazol and Edaravone on Focal Cerebral Ischemia-Reperfusion Injury 3

1 Materials and Methods 1.1 Experimental Animals

Sprague-Dawley (SD) rats, male, SPF-grade, weighing 250-280 g.

1.2 Test Drugs

Cilostazol and edaravone were the same as in Example 1.

1.3 Experimental Method

The experimental animals were divided into 4 groups, cilostazol group (15 mg/kg), edaravone group (3 mg/kg), cilostazol and edaravone composition group (18 mg/kg, cilostazol:edaravone=5:1, cilostazol 15 mg/kg+edaravone 3 mg/kg) and model group. After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

The establishment of the focal cerebral ischemia-reperfusion model, the determination of the area of cerebral infarction, the analysis of synergy of the composition and the data statistics method were the same as in Example 1.

2 Experimental Results

The effects on the area of cerebral infarction are shown in Table 3. The experimental results show that the administration of cilostazol at 15 mg/kg, edaravone at 3 mg/kg and the composition (cilostazol 15 mg/kg+edaravone 3 mg/kg) can significantly reduce the area of cerebral infarction in animals (p=0.007, p=0.029, p=0.000). The calculation result of synergy was q=1.38, indicating that the combined use of the two drugs had a synergistic effect.

TABLE 3

Effects of combined administration of cilostazol and edaravone on the area of cerebral infarction

| Group | Number of animals | Area of cerebral infarction (%) |
|---|---|---|
| Model group | 11 | 39.41 ± 9.56 |
| Cilostazol group | 11 | 27.26 ± 9.74** |
| Edaravone group | 12 | 31.24 ± 6.83* |
| Group of composition of cilostazol and edaravone in 5:1 | 12 | 17.08 ± 6.26*** |

Mean ± standard deviation,
*p < 0.05,
**p < 0.01,
***p < 0.001, compared with the model group.

Example 4 Effects of Cilostazol/Edaravone (1:5, 1:2.5, 1:1) on Focal Cerebral Ischemia-Reperfusion Injury 1 Materials and Methods 1.1 Experimental Animals Sprague-Dawley (SD) rats, male, SPF-grade, weighing 250-280 g.

1.2 Test Drugs

Cilostazol and edaravone were the same as in Example 1.

1.3 Experimental Method

The experimental animals were divided into 4 groups, a model group and three groups of compositions of cilostazol/edaravone (respectively a group of cilostazol 1.67 mg/kg+edaravone 8.33 mg/kg in 1:5; a group of cilostazol 2.86 mg/kg+edaravone 7.14 mg/kg in 1:2.5; a group of cilostazol 5 mg/kg+edaravone 5 mg/kg in 1:1, and each composition was administered at a total amount of 10 mg/kg). After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

The establishment of the focal cerebral ischemia-reperfusion model, the determination of the area of cerebral infarction and the data statistics method were the same as in Example 1.

2 Experimental Results

The effects on the area of cerebral infarction are shown in Table 4. The experimental results show that the combined administration of cilostazol/edaravone in 1:5, 1:2.5 and 1:1 can significantly reduce the area of cerebral infarction in animals (p<0.001).

TABLE 4

Effects of compositions of cilostazol/edaravone on the area of cerebral infarction

| Group | Number of animals | Area of cerebral infarction (%) |
|---|---|---|
| Model group | 12 | 38.75 ± 8.79 |
| Group of cilostazol/edaravone in 1:5 | 12 | 21.91 ± 8.89*** |
| Group of cilostazol/edaravone in 1:2.5 | 12 | 19.46 ± 9.39*** |

TABLE 4-continued

| Effects of compositions of cilostazol/edaravone on the area of cerebral infarction | | |
|---|---|---|
| Group | Number of animals | Area of cerebral infarction (%) |
| Group of cilostazol/ edaravone in 1:1 | 13 | 15.72 ± 8.28*** |

Mean ± standard deviation,
***p < 0.001, compared with the model group.

Example 5 Effects of Cilostazol/Edaravone (1:1, 2.5:1, 5:1) on Focal Cerebral Ischemia-Reperfusion Injury 1 Materials and METHODS 1.1 Experimental Animals Sprague-Dawley (SD) rats, male, SPF-grade, weighing 250-280 g.

1.2 Test Drugs

Cilostazol and edaravone were the same as in Example 1.

1.3 Experimental Method

The experimental animals were divided into 4 groups, a model group and three groups of compositions of cilostazol/edaravone (respectively a group of cilostazol 5 mg/kg+edaravone 5 mg/kg in 1:1, a group of cilostazol 7.14 mg/kg+edaravone 2.86 mg/kg in 2.5:1; a group of cilostazol 8.33 mg/kg+edaravone 1.67 mg/kg in 5:1, and each composition was administered at a total amount of 10 mg/kg). After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

The establishment of the focal cerebral ischemia-reperfusion model, the determination of the area of cerebral infarction and the data statistics method were the same as in Example 1.

2 Experimental Results

The effects on the area of cerebral infarction are shown in Table 5. The experimental results show that the combined administration of cilostazol/edaravone in 1:1, 2.5:1 and 5:1 can significantly reduce the area of cerebral infarction in animals (p=0.000, p=000, p=001).

TABLE 5

| Effects of compositions of cilostazol/edaravone on the area of cerebral infarction | | |
|---|---|---|
| Group | Number of animals | Area of cerebral infarction (%) |
| Model group | 12 | 40.52 ± 8.64 |
| Group of cilostazol/ edaravone in 1:1 | 13 | 17.11 ± 8.94*** |
| Group of cilostazol/ edaravone in 2.5:1 | 12 | 22.90 ± 11.37*** |
| Group of cilostazol/ edaravone in 5:1 | 12 | 24.54 ± 12.10** |

Mean ± standard deviation,
**p < 0.01,
***p < 0.001, compared with the model group.

Example 6 Effects of Cilostazol/Edaravone (1:1, 1:2.5, 1:1) on Focal Cerebral Ischemia-Reperfusion Injury in Mice 1 Materials and Methods 1.1 Experimental Animals C57BL/6J mice, male, SPF-grade, 8 week-old.

1.2 Test Drugs

Cilostazol and edaravone were the same as in Example 1.

1.3 Experimental Method

The experimental animals were divided into 4 groups, a model group and three groups of compositions of cilostazol/edaravone (respectively a group of cilostazol 3.33 mg/kg+edaravone 16.67 mg/kg in 1:5; a group of cilostazol 5.71 mg/kg+edaravone 14.29 mg/kg in 1:2.5; a group of cilostazol 10 mg/kg+edaravone 10 mg/kg in 1:1, and each composition was administered at a total amount of 20 mg/kg). After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

Establishment of focal cerebral ischemia-reperfusion model: The mouse focal cerebral ischemia-reperfusion model was established by internal carotid artery suture method. An anesthetized mouse was fixed on an operating table in a supine position. The neck of the mice was cut at the midline, and the subcutaneous tissue was bluntly separated. The right common carotid artery, external carotid artery, and internal carotid artery were separated. The external carotid artery was inserted with a suture line, which was passed through the bifurcation of the common carotid artery into the internal carotid artery, and then was inserted slowly until reaching slight resistance (approximately 10 mm from the bifurcation), so as to block all blood supply to the cerebral artery. 60 minutes after cerebral ischemia on the right side, the suture line was gently pulled out to restore the blood supply for reperfusion. The mice were placed in clean feed, and their general condition and respiration were observed until they woke up from anesthesia. The mice were provided with food and water, and commonly reared.

The determination of the area of cerebral infarction and the data statistics method were the same as in Example 1.

2 Experimental Results

The effects on the area of cerebral infarction are shown in Table 6. The experimental results show that the combined administration of cilostazol/edaravone in 1:5, 1:2.5 and 1:1 can significantly reduce the area of cerebral infarction in animals (p<0.001, p<0.012, p<0.001).

TABLE 6

| Effects of compositions of cilostazol/edaravone on the area of cerebral infarction | | |
|---|---|---|
| Group | Number of animals | Area of cerebral infarction (%) |
| Model group | 12 | 36.24 ± 9.46 |
| Group of cilostazol/ edaravone in 1:5 | 13 | 22.49 ± 8.76*** |
| Group of cilostazol/ edaravone in 1:2.5 | 12 | 21.12 ± 11.04** |

TABLE 6-continued

Effects of compositions of cilostazol/edaravone on the area of cerebral infarction

| Group | Number of animals | Area of cerebral infarction (%) |
|---|---|---|
| Group of cilostazol/ edaravone in 1:1 | 13 | 16.75 ± 8.44*** |

Mean ± standard deviation,
**$p < 0.01$,
***$p < 0.001$, compared with the model group.

Example 7 Effects of Cilostazol/Edaravone (1:1, 2.5:1, 5:1) on Focal Cerebral Ischemia-Reperfusion Injury in Mice 1 Materials and Methods 1.1 Experimental Animals C57BL/6J mice, male, SPF-grade, 8 week-old.

1.2 Test Drugs

Cilostazol and edaravone were the same as in Example 1.

1.3 Experimental Method

The experimental animals were divided into 4 groups, a model group and three groups of compositions of cilostazol/edaravone (respectively a group of cilostazol 10 mg/kg+edaravone 10 mg/kg in 1:1; a group of cilostazol 14.29 mg/kg+edaravone 5.71 mg/kg in 2.5:1; a group of cilostazol 16.67 mg/kg+edaravone 3.33 mg/kg in 5:1, and each composition was administered at a total amount of 20 mg/kg). After the cerebral ischemia model was established, the animals were assigned to each group in a single-blind manner with equal probability. After reperfusion, the animals were immediately administered intravenously with the drugs once. The animals in the model group were administered with an equal volume of normal saline. The animals were sacrificed 24 hours after cerebral ischemia, and their brains were taken out, stained, and photographed for determining the area of cerebral infarction.

The establishment of focal cerebral ischemia-reperfusion model was the same as in Example 6, and the determination of the area of cerebral infarction and the data statistics method were the same as in Example 1.

2 Experimental Results

The effects on the area of cerebral infarction are shown in Table 7. The experimental results show that the combined administration of cilostazol/edaravone in 1:1, 2.5:1 and 5:1 can significantly reduce the area of cerebral infarction in animals ($p<0.001$).

TABLE 7

Effects of compositions of cilostazol/edaravone on the area of cerebral infarction

| Group | Number of animals | Area of cerebral infarction (%) |
|---|---|---|
| Model group | 13 | 39.06 ± 7.90 |
| Group of cilostazol/ edaravone in 1:1 | 13 | 15.58 ± 8.95*** |
| Group of cilostazol/ edaravone in 2.5:1 | 12 | 21.23 ± 10.84*** |
| Group of cilostazol/ edaravone in 5:1 | 12 | 23.88 ± 11.90*** |

Mean ± standard deviation,
***$p < 0.001$, compared with the model group.

The use of a composition comprising cilostazol in cerebrovascular diseases provided by the present invention has been described in detail above. The principle and embodiments of the present invention are illustrated herein by using specific examples. The description of the above examples is only used to help understand the method and core idea of the present invention. It should be noted that for those skilled in the art, without departing from the principle of the present invention, several improvements and modifications can be made to the present invention, and these improvements and modifications also fall within the protection scope of the claims of the present invention.

The invention claimed is:

1. A composition comprising the following components:

component (I), cilostazol, a pharmaceutically acceptable salt, or a prodrug molecule thereof; and component (II), edaravone, or a drug with an active ingredient of edaravone;

wherein the component (I) and the component (II) are in a weight ratio of 1:5-5:1.

2. The composition according to claim 1, wherein the component (I) and the component (II) are in a weight ratio of 1:2.5-2.5:1.

3. The composition according to claim 1, wherein the component (I) and the component (II) are in a weight ratio of 1:1-2.5:1.

4. The composition according to claim 1, wherein the component (I) and the component (II) are in a weight ratio of 1:1, 5:1, 2.5:1, 1:2.5 and/or 1:5.

5. A drug, comprising the composition according to claim 1, and a pharmaceutically acceptable adjuvant.

6. A method for treating cerebrovascular diseases, comprising administering the composition according to claim 1 to a subject in need thereof.

7. A method for treating cerebrovascular diseases, comprising administering the drug according to claim 5 to a subject in need thereof.

8. The method according to claim 6, wherein the cerebrovascular disease is selected from ischemic cerebrovascular disease.

9. The method according to claim 8, wherein the ischemic cerebrovascular disease is selected from ischemic stroke.

10. The method according to claim 7, wherein the cerebrovascular disease is selected from ischemic cerebrovascular disease.

11. The method according to claim 10, wherein the ischemic cerebrovascular disease is selected from ischemic stroke.

* * * * *